United States Patent [19]

Guo et al.

[11] Patent Number: 5,824,841

[45] Date of Patent: Oct. 20, 1998

[54] TETRAPLOID SHELLFISH

[75] Inventors: Ximing Guo, Glassboro; Standish K. Allen, Jr., Mauricetown, both of N.J.

[73] Assignee: Rutgers, The State University of New Jersey, New Brunswick, N.J.

[21] Appl. No.: 895,077

[22] Filed: Jul. 16, 1997

Related U.S. Application Data

[63] Continuation of Ser. No. 316,279, Sep. 30, 1994, abandoned, which is a continuation-in-part of Ser. No. 184,838, Jan. 21, 1994, abandoned.

[51] Int. Cl.$^6$ .......................... A01K 61/00; A01K 67/00
[52] U.S. Cl. ..................... 800/2; 800/DIG. 4; 119/234; 119/236
[58] Field of Search ................................ 800/2, DIG. 4; 119/234, 236

[56] References Cited

FOREIGN PATENT DOCUMENTS

92106666.X   8/1992   China .

OTHER PUBLICATIONS

S Gendreau et al (1990) Aquaculture 90: 229–238 (abstract only).

LB Stephens et al (1988) J Shellfish Research 7: 550–551 (abstract only).

X Guo et al (1989) J Shellfish Research 8: 321 (abstract only).

X Guo et al (1990) J Shellfish Research 10: 236 (abstract only).

X Guo et al (1992) Biol Bull Woods Hole 183: 381–386 (abstract only).

X Guo et al (1994) J Shellfish Research 13: 193–198 (abstract only).

Allen. Jr, SK 1986A. Genetic Manp. Critical rev. of method and perf. in shellfish. In K Tiews in Aquaculture, Proc. of a World Symposium, Schriften der Bundesforschungsanstalt fur Fischerei Hamburg Band 18/19, Berlin.

Allen, Jr. SK 1986b. Gametogensis in 3 species of triploid shellfish *Mya arenaria C. gigas* & *C. virginica*. In K Tiews (ed) Sel. Hybridization and Gen. Eng. in Aquaculture, Proc. of a World Symp. Schriften der Bundesforschungsanstalt fur Fish. Hamb. Band 18/19, Berlin.

Allen, Jr., S.K. et al. 1990. Performance of triploid Pacific oysters, *C. gigas*, Gametogensis, Can J. Fish, Aquat. Sci. 47: 12–13–1222.

Beaumont, A.R. and J.E. Fairbrother 1991. Ploidy manipulation in molluscan shellfish: a review. Journal of Shellfish Research 10: 1–18.

Breese, W.K. and R.E. Malouf. 1975. Hatchery manual for the Pacific oyster. Oregon State University of Sea Grant Program, Rep. No. ORESU–H–002.23 pp.

Castagna, M. 1983. Review of reent bivale culture methods. J. World Maricul. Soc. 14:567–575.

Dupuy, J.L., et al. 1997. Manual for the design and operation of an oyster seed hatchery for the American oyster *virginica*. pp. 24–50.

Gaffney, P.M. and S.K. Allen, Jr. 1993. Hybridization among *Crassostrea* species: a review. Agriculture 116: 1–13.

Galtsoff, P.S. 1964. The American Oyster, *virginica* Gmelin. Fishery Bulletin, vol. 64, US Department of the the Interior, Washington, D.C., U.S.A. pp. 1–4; 313.

Gilbert, S.F. 1988. Development biology (2nd edition). Sinauer Associates, Inc. Sunderland, Massachusetts, U.S.A., p. 788.

Guo, X., 1991, Studies on Tetraploid Induction in the Pacific Oyster, *C. gigas*. Ph.D. Dissertation, University of Washington, Seattle, USA pp. 1–8.

(List continued on next page.)

*Primary Examiner*—Bruce R. Campell
*Attorney, Agent, or Firm*—Fish & Richardson P.C.

[57] ABSTRACT

Provided by this invention are novel tetraploid mollusks, including oysters, scallops, clams, mussels and abalone. Also, provided are a method for producing the tetraploid mollusks and a method for producing triploid mollusks by mating the novel tetraploid mollusks with diploid mollusks.

36 Claims, 2 Drawing Sheets

OTHER PUBLICATIONS

Komaru, A. and K.T. Wada. 1988. Gametogenesis and growth of induced triploid scallops *Chlamys nobilis*. Nippon Suisan Gakkaishi 55: 447–452.

Lee, M.M. 1988. Abnormal gametogensis in triploid American oysters *C. virginica*. J. Shellfish. Res. 7:201–202.

Mackie, G.L. 1984. Bivalves In A.S. Tompa, N.H. Verdonk, and J.A.M. van den Biggelaar (eds.) The Mollusca. vol. 7: Reproduction. Academic Press, NY pp. 351–418.

Morton, J.E. 1979. Mollusks. Hutchinson & Co., Ltd., London. p. 141.

Nell, J.A., et al. 1994. Studies on triploid oysters in Australia. The farming potential of triploid Sydney rock oysters *Saccostrea commercialis* (Iredale and Roughley) Aquaculture 126:2443–255.

Strathmann, M.F. 1987. Reproduction and Development of Marine Invertebrates of the Northern Pacific Coast, University of Washington Press, Seattle, p. 310.

Walne, P. 1974. Culture of Bivalve Mollusks. 50 Years Experience at Conway. Fishing News (Books Ltd., West Byfleet, Surry, UK pp. 50–75.

Guo et al., "Viable tetraploids in the Pacific oyster *(Crassostrea gigas Thunberg)* produced by inhibiting polar body 1 in eggs from triploids", Molecular Marine Biology and Biotechnology (1994) 3(1) pp. 42–50.

Guo et al., Genetic Consequences of Blocking Polar Body I with Cytochalasin B. in Fertilized Eggs of the Pacific Oyster, *Crassostrea gigas*: I. Ploidy of Resultant Embryos, Biol. Bull. 183: 381–389 (Dec. 1992).

Scarpa, J. et al., Induction of tetraploidy in mussels by suppression of polar body formation, Nippon Suisan Gakkaishi 50 (12). 1993. 2017–2023 (English Abstract).

TETRAPLOID SHELLFISH

CROSS-REFERENCE TO RELATED APPLICATION

This is a continuation of application Ser. No. 08/316,279 filed Sep. 30, 1994, now abandoned, which is a continuation-in-part of U.S. application Ser. No. 08/184,838, filed Jan. 21, 1994, now abandoned.

TECHNICAL FIELD

The present invention relates to the production of viable tetraploid shellfish including oysters. Said tetraploidy is produced by use of chromosome set manipulation techniques.

BACKGROUND OF THE INVENTION

Most sexually reproducing animals have two sets of chromosomes and hence are called diploids. Meiosis is the process that reduces the chromosome number by one-half so as to keep the chromosome number from doubling with each generation. It is a two-step process, whereby one diploid cell gives rise to four haploid cells, each having one set of chromosomes. One or all four of these haploid cells may mature into functional egg or sperm cells, otherwise known as gametes.

Tetraploids in animals (namely those having four sets of chromosomes) in general are important for various purposes including production of triploids, hybridization and other breeding programs. However, previous attempts to produce viable tetraploidy in mollusks including oysters have not been successful. It has been speculated that part of the reason for the inviability of tetraploids induced in diploid eggs may be due to a cell-number deficiency caused by the cleavage of normal diploid egg cells by a large tetraploid nucleus. It is very desirable to develop a method whereby tetraploid zygotes are produced in mollusks which are viable through the usual hatchery process and mature into full-grown mollusks so that a reliable supply of tetraploid mollusks is provided, which in turn can be used, for instance, for the commercial scale production of triploid mollusks.

The present invention will be illustrated below by use of the Pacific oysters, namely, *Crassostrea gigas* Thunberg.

In the case of the Pacific oysters, although tetraploid embryos have been produced by several methods including mitosis I blocking (Guo 1991), polar body I blocking (Guo et al. 1992a,b), blastomere fusion (Guo 1991) and gynogenesis (Guo et al. 1993), all in eggs from diploids, the produced embryos have not survived beyond the metamorphosis. As mentioned above, it has been speculated that the inviability of the induced tetraploids may be due to a cell-number deficiency in the embryos caused by the cleavage of a normal egg with a large tetraploid nucleus. Eggs from triploid oysters, on the other hand, are significantly larger than those from normal diploid oysters (Stephens and Downing, 1989).

Triploid Pacific oysters are now commercially available (Allen, 1988). Such triploid Pacific oysters are known to have certain commercial advantages over normal diploid oysters including preferred taste (Allen and Downing, 1991) especially during the normal reproductive period of the diploids and improved growth rate (Allen, 1988). At the present time, such commercial triploid Pacific oysters are produced from normal diploid oysters by use of certain chromosome set manipulation techniques whereby the meiotic events in the oocyte are manipulated such that the oocyte retains the second polar body within itself instead of releasing it during the second meiotic division (Allen, 1988). Thus, such triploid oysters may be called induced triploids. In contrast to this, as one of the direct benefits arising from the present invention, mated triploids can be produced by simply mating a mature tetraploid with a normal diploid.

SUMMARY OF THE INVENTION

According to the present invention, the first polar body in the eggs of a triploid mollusk is manipulated so as to produce a viable tetraploid mollusk (shellfish). Typically, eggs are obtained from a triploid female by dissection and thereafter rinsed with filtered sea water. The eggs are fertilized with sperm obtained from a normal diploid male. At a suitable point in time after the fertilization of the eggs (5 minutes post-fertilization, for instance), a process for blocking the release of polar body I from the eggs is carried out for a suitable length of time. Subsequently, the eggs are incubated under standard hatchery conditions. In a preferred embodiment of this invention, said process for blocking the polar body I (PB1) is carried out by treating the fertilized eggs with cytochalasin B (CB) or other blocking agents dissolved in filtered sea water at a suitable concentration, but the process may also be carried out by administering a thermal or hydrostatic shock to the fertilized eggs. By virtue of this invention, viable tetraploid shellfish which can grow to maturity are produced.

DETAILED DESCRIPTION OF INVENTION

Figure 1A:
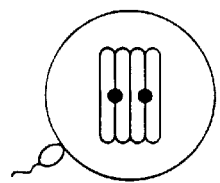
FIG. 1 schematically depicts the normal process of meiosis and fertilization observed with normal diploid oysters.
Figure 1B:
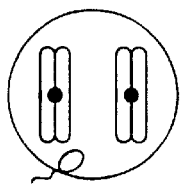
Figure 1C:
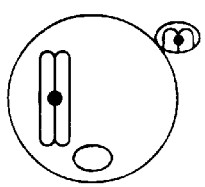
Figure 1D:
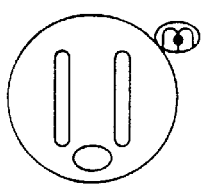
Figure 1E:
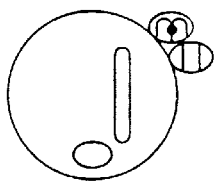
Figure 1F:
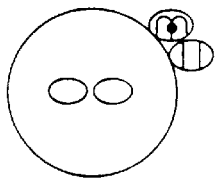
Figure 1G:
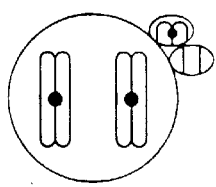
Figure 1H:
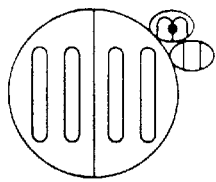

The present invention is applicable to mollusks in general. However, a detailed description of the invention will be illustrated below by use of Pacific oysters (*Crassostrea gigas* Thunberg), which is a bivalve. A bivalve is any mollusk having a shell consisting of two parts or valves, hinged together by an elastic ligament.

In order to aid the understanding of the present invention, brief definitions of certain technical terms are presented at the end of the text of this specification. The definitions, however, are not intended to be limiting or to supercede the usual definitions generally accepted by people skilled in the art.

The Pacific oyster is a benthic marine bivalve naturally distributed along the coasts of Japan, Korea and China. Pacific oyster is a filter feeder that feeds primarily on microalgae and small organic debris. It is diecious, and the fertilization occurs externally. No secondary sexual characteristics can be identified, and sex can be determined only by examination of the gonadal tissue. During the spawning season, the Pacific oyster may devote over half of its body weight to the production of gametes (Perdue, 1983). An average market-size female Pacific oyster may produce 50–100 million eggs (Quayle, 1988). The newly released eggs of the Pacific oyster are pear-shaped, and upon fertilization, they assume a spherical form with a diameter of about 50 $\mu$m. The fertilized eggs will go through rapid change and hatch as swimming trochophores within 6–7 hours post-fertilization at 25° C. At about 24 hours post-fertilization, the trochophores form two shells and appear as "D" shaped larvae. The free-swimming stage of the larvae may last for about 3–5 weeks, during which they can be widely spread by currents. At the end of the free-swimming stage when they reach about 0.3 mm in size, the larvae metamorphose and permanently cement themselves to a hard surface. Depending on the temperature and food availability, sexual maturation is reached at 1–2 years of age.

The Pacific oyster, like all species of the genus Crassostrea, normally has a diploid number of 20 chromosomes. Mature eggs of the Pacific oyster are arrested at the prophase of the first meiotic division (Lu, 1986). Ten synapsed tetrads are visible in newly fertilized eggs by microscopic observation. After fertilization or activation, the ten tetrads normally will go through two meiotic divisions and release two polar bodies, namely, polar body I which contains 20 dyads and polar body II which contains 10 chromatids. The remaining 10 chromatids in the oocyte will unite with the 10 chromatids from the sperm to form a diploid zygote. The above-mentioned normal process of meiosis and fertilization observed with normal diploid oysters is depicted schematically in FIG. 1.

Referring to FIG. 1 and the individual steps (a) through (h) depicted therein: (a) prior to meiosis, the two sets of chromosomes double to form two sets of duplicated chromosomes; duplicated chromosomes are held together by a centromere; (b) fertilization activates the egg and meiosis resumes; (c) the first meiotic division results in the elimination of an entire duplicated set of chromosomes in the first polar body; (d) the second meiotic division divides the remaining chromosomes that were held together by the centromere; (e) one set is eliminated in the second polar body; (f) the remaining haploid set from the egg and that of the sperm unite in a process called syngamy which restores diploidy to the cell; (g) the diploid set of chromosomes duplicate; (h) division gives rise to a diploid embryo.

According to this invention, tetraploid oysters are produced from a triploid female and a diploid male with the aid of chromosome set manipulation. To this end, triploid females are conditioned by placing them in an environment with high temperature and abundant food. It is preferable that the conditioning be started at the earliest stage of gametogenesis immediately following winter dormancy. As mentioned earlier, triploid oysters are now available on a commercial scale. They are typically produced from diploid oysters by blocking the release of polar body II from fertilized eggs during the meiosis. (As a result of the present invention a new route has been opened for the production of triploid oysters which has certain advantages over the prior art route. However, for the purpose of accomplishing the present invention based on the prior art taken as the starting line, female triploid oysters of the prior art are used as a starting material. It will become apparent later that a new type of triploid oysters can be produced by mating the tetraploid oyster (female) of this invention with a normal diploid male oyster. Such new type of triploid oysters which are produced by natural mating not involving any artificial event in the fertilization process are expected to have certain advantages over the prior art triploid oysters which are produced by an artificial fertilization process involving polar body II blocking. See below for further discussion.) Triploid animals are individually examined by flow cytometry (Guo, 1991) prior to spawning in order to confirm their ploidy.

As a next step, eggs are collected from the triploid female by dissection (strip spawning). The eggs are rinsed with filtered sea water and retained on a suitable screen such as a 25 µm screen.

The eggs are then fertilized with sperm obtained from a normal diploid male. The amount of sperm used for the fertilization is typically about 10 sperm cells per 1 egg cell.

Suppression of the release of polar body I from the fertilized eggs must be started at a suitable point in time after the fertilization. The suppression of PB1 can be accomplished by applying a thermal or hydrostatic shock, or with the aid of a chemical agent such as cytochalasin B or 6-dimethylaminopurine. It is preferable in this invention to accomplish said suppression of PB 1 with the aid of cytochalasin B (CB). The duration of the chemical treatment of fertilized eggs needs to be adjusted in order to obtain optimal results. Typically, the duration of the CB treatment corresponds to about 60–80% of the statistical average time it takes for half of untreated triploid eggs to release their polar body I under the corresponding condition in the absence of the chemical agent. In most cases said statistical average time can be determined by microscopic examination, and at 25° C. it is about 25 minutes in the Pacific oysters. Thus, the CB treatment lasts typically for about 15–20 minutes at 25° C. The starting time of the CB treatment needs also to be adjusted in order to obtain optimal results. Typically the starting time of the CB treatment is about 5 minutes post-fertilization.

After the PB1 blocking process has been carried out, the eggs are removed from the influence of the process and subjected to subsequent steps which are standard to the usual shellfish hatchery industry.

The following examples are presented in order to illustrate the present invention.

EXAMPLE

Triploid Pacific oysters used in this study were two years old and produced by blocking the release of PB2. Triploid animals were individually confirmed by flow cytometry prior to spawning. Gametes were obtained by strip-spawning. Eggs were passed through an 85 µm screen to remove the large tissue debris and rinsed on a 25 µm screen. All fertilization and treatment were conducted at 25°–28° C. using filtered (2 µm) seawater. The salinity of the seawater used in this study was about 20–22 ppt.

Eggs from triploids were fertilized with haploid sperm from diploids. After fertilization the eggs were divided into two groups: the TD and TDCB groups. hi the TD group, fertilized eggs were not treated with any chemical and cultured as a control group. In the TDCB group, the fertilized eggs were treated with cytochalasin B (CB) to block the release of PB1. CB was prepared in dimethyl sulfoxide (DMSO) and added to fertilized eggs at a final concentration of 0.5 mg/liter with 0.5% DMSO. The CB treatment started at 5 minutes post-fertilization (PF) and lasted for 15 minutes. After the CB treatment, eggs were rinsed with DMSO-seawater (1%) and cultured at a density of 65 eggs/ml. Three replicates were made using three pairs of oysters as parents. Because of the low fecundity of triploid females and the anticipated low survival of experimental groups, all available eggs were used, and the number of eggs in three replicates were not standardized. Also, more eggs were assigned to the TDCB groups to ensure survival of tetraploids, but the culture density was maintained approximately the same.

Percent division in both TD and TDCB groups were determined at 90–120 minutes PF. Survival of divided embryos to the D-stage (Day 1), Day 7 and spat (Day 35) were recorded in both groups. Also at those sampling dates, the ploidy composition of the surviving larvae were determined by flow cytometry.

At three months PF, surviving oysters were sampled for body weight and chromosome counts. For chromosomal analysis, oysters were first treated with colchicine (0.005%) for 12 hours with intensive feeding. Visceral parts of oysters were separated from shells and weighed. The whole body was then chopped and fixed in an acetic acid/methanol mixture (1:3). Appropriate amounts of the fixed samples were poured into slides and air-dried. The slides were stained with Leishman's stain. A minimum of ten metaphases which showed no obvious sign of chromosome loss were counted for each oyster. Only those individuals whose chromosome number was confidently determined were included in the analysis. Oysters with 20, 30 and 40 chromosomes were classified as diploid, triploid and tetraploid, respectively.

On the average, eggs from triploids were 15% larger in diameter than those obtained from diploids, which translated into a 54% increase in volume. The number of eggs obtained from triploids varied among the three replicates. Thus, the three triploid females produced 8.2, 0.4 and 0.7 million eggs respectively. The CB treatment did not have any significant effect on the early mitotic divisions, and the percent divisions were approximately the same in the TD and TDCB groups. See Table 1.

Survival rate of the divided eggs to the D-stage (24 hours PF) varied among the three replicates (Table 1). In Replicate 1, the TDCB group had a lower percent of survival than the TD group. In Replicate 2, the two groups were approximately the same. In Replicate 3, however, the TDCB group had a higher percent of survival than the TD group. When compared at later stages, it was clear that the TDCB groups ultimately had higher survival rates than the corresponding TD groups. In both Replicates 2 and 3, the TDCB group exhibited a higher survival than the TD group at Day 7, although there were no survivors at Day 35 in either the TD or TDCB group in both replicates. In Replicate 1, the TDCB group showed a lower survival than the TD group at Day 7. After metamorphosis and settlement, however, the TDCB1 group (namely, the TDCB group from Replicate 1) produced significantly more spat than the TD1 group (namely, the TD group from Replicate 1). A total of 2,500 spat were harvested from TDCB1 representing 0.0738% of the divided eggs, whereas only two spat were obtained from TD1, representing 0.0003% of the divided eggs.

At 24 hours PF, the dissociated embryos in the TD groups consisted primarily of 2.5 n aneuploid cells (n being the haploid number, namely 10 in this case) as analyzed by flow cytometry. In the TDCB groups, two aneuploid cell populations were evident. One population fell between triploid and tetraploid, and the other fell between tetraploid and pentaploid. Euploid peaks were not apparent at 24 hours PF. At Day 7, cells derived from the surviving larvae in the TD groups were still primarily aneuploids, but the peak at 2.5 n was no longer evident. Instead, the aneuploid peak in the TD groups was inclined toward diploid. In the TDCB groups, the cells of the surviving larvae at Day 7 were predominantly tetraploids or aneuploids close to tetraploids. There was a small peak of triploids or aneuploids close to triploid.

At Day 13, no larvae remained in the TD and TDCB groups of Replicates 2 and 3. Survivors in TD1 were too few to be sampled for flow cytometry. A sample of eyed larvae from TDCB 1 was collected on Day 13 and an aggregate of about 100 were dissociated into a suspension of single cells for flow cytometry. Our estimate of the proportion of cells in 2 n, 3 n and 4 n class was 4%, 16% and 80%, respectively. At Day 22, 12 metamorphosed larvae from TDCB1 were analyzed: Eight tetraploids (67%), two triploids (17%) and two mosaics (17%) were found. In TD1, the surviving two spat were sacrificed on Day 35: one was diploid and the other was triploid. Because it was difficult to detect small differences in the DNA content by flow cytometry, the euploids listed here (from TDI) might include aneuploids plus or minus a few chromosomes.

There was virtually no post-settlement mortality. At three months PF, oysters from TDCB1 reached 1–4 cm in length. Thirty-one oysters from TDCB 1 were sampled for body weight and chromosome count. Unambiguous chromosome counts were obtained from thirty oysters, and the other oyster did not have enough scorable metaphases and was excluded from the analysis. Among the thirty oysters, one had 20 chromosomes and one had 30 chromosomes, and they were classified as diploid (3.3%) and triploid (3.3%), respectively. Twenty oysters had exactly 40 chromosomes and were classified as tetraploids (66.7%). Seven oyster were aneuploids (23.3%) with 21, 31, 32, 33, 38(2), 39 and 41 chromosomes. One oyster was mosaic with 73% of the cells having 32 chromosomes and 27% having 40 chromosomes.

Tetraploid oysters had an average body weight (visceral) of 284 mg ranging from 15 mg to 610 mg (see Table 2). On the average, aneuploid oysters were significantly ($p<0.05$) smaller than tetraploids. However, one of the aneuploid oysters with 38 chromosomes weighed 479 mg which is the fourth largest oyster in the group, and the largest by whole body weight (with shells). Both the diploid and the triploid oysters were small compared with tetraploids.

TABLE 1

Number of eggs used, percent divisions and survival of divided zygotes to D-stage (Day 1), Day 7 and Spat (Day 35) in experimental groups of three replicates.

| Group | Eggs (×1000) | Divisions (%) | D-stage (%) | Day 7 (%) | Spat (%) |
| --- | --- | --- | --- | --- | --- |
| TD1 | 700 | 86.4 | 21.7 | 5.7 | 0.0003 |
| TDCB1 | 3998 | 84.6 | 5.4 | 2.1 | 0.0739 |
| TD2 | 144 | 79.3 | 5.1 | 0.3 | 0 |
| TDCB2 | 217 | 70.8 | 5.7 | 1.1 | 0 |
| TD3 | 217 | 87.7 | 29.5 | 1.0 | 0 |
| TDCB3 | 444 | 89.2 | 35.2 | 1.2 | 0 |

TABLE 2

Ploidy categories and body weight (mg) of three-month old Pacific oysters produced by inhibiting polar body I in eggs from triploids fertilized with haploid sperm.

| Ploidy | Number (%) | Body Weight (SE) |
| --- | --- | --- |
| Diploid | 1(3.3) | 65 |
| Triploid | 1(3.3) | 92 |
| Tetraploid | 20(66.7) | 284(33) |
| Aneuploid | 7(23.3) | 160(49) |
| Mosaic | 1(3.3) | 62 |
| Total | 30(100) | 237(28) |

EXAMPLE 2

Tetraploids of blue mussels *Mytitus edulis* are produced following essentially the procedure of Example 1 using corresponding eggs from triploids and haploid sperm from diploids.

EXAMPLE 3

Tetraploids of pearl oysters *Pinctada magaratifera* are produced following essentially the procedure of Example 1 using corresponding eggs from triploids and haploid sperm from diploids.

EXAMPLE 4

Tetraploids of Kumomoto oyster *Crassostrea sikamai* are produced following essentially the procedure of Example 1 using eggs from triploids and haploid sperm from diploids.

EXAMPLE 5

Tetraploids of Suminoe oyster *Crassostrea rivularis* are produced following essentially the procedure of Example 1 using corresponding eggs from triploids and haploid sperm from diploids.

EXAMPLE 6

Tetraploids of American oyster *Crassostrea virginica* are produced following essentially the procedure of Example 1 using eggs from triploids and haploid sperm from diploids.

EXAMPLE 7

Tetraploids of the bay scallop *Argopectin irradians* are produced following essentially the procedure of Example 1 using corresponding eggs from triploids and haploid sperm from diploids.

EXAMPLE 8

Tetraploids of the genus Chlamys, especially Chinese scallop *Chlamys farrari*, are produced following essentially the procedure of Example 1 using corresponding eggs from triploids and haploid sperm from diploids.

EXAMPLE 9

Tetraploids of Manila clam *Tapes philippinarum* are produced following essentially the procedure of Example 1 using corresponding eggs from triploids and haploid sperm from diploids.

EXAMPLE 10

Tetraploids of genus Patinopecten, especially Japanese scallop *Patinopecten yessoensis*, are produced following essentially the procedure of Example 1 using corresponding eggs from triploids and haploid sperm from diploids.

EXAMPLE 11

Tetraploids of gastropod mollusks, especially abalone, genus Haliotus, are produced following essentially the procedure of Example 1 using corresponding eggs from triploids and haploid sperm from diploids.

EXAMPLE 12

The data of the example show that tetraploids of this invention are very useful and effective for the production of triploids. Like normal diploids, tetraploid oysters mature at one year of age. At maturation, tetraploid Pacific oysters (*Crassostrea gigas* Thunberg) were sampled. They were either females or males with an approximately normal sex ratio. In contrast to triploids which had severely reduced fecundity, tetraploids exhibited fecundities similar to those of diploids. Cross matings between tetraploids and diploids were made.

All spat from tetraploids x diploids (and recriprocal) crosses examined so far were triploids as analyzed by flow cytometry.

All four possible crosses were made between diploids (D) and tetraploids (T): DD, DT, TD and TT (female type listed first). The diploid female had 8.9 million eggs, and the tetraploid female had 6.4 million eggs. Level of fertilization was good in all groups, ranging from 92.3 to 97.8% (Table 1). Compared with normal diploid control (DD), the number of fertilized eggs survived to spat stage was good in DT and TD crosses. The TT crosses had very low survival.

At 50 days post-fertilization, oysters from DD, DT and TD crosses (30 oysters per group) were sampled for ploidy determination by flow cytometry. All 30 oysters from DD were diploids. All 60 oysters from DT and TD crosses were triploids. Three oysters analyzed from TT crosses were tetraploids.

TABLE 1

Level of fertilization, number of eggs fertilized, and cumulative survival to D and spat stage.

| Group | Level of Fertilization (%) | Number of Eggs Fertilized (×10$^6$) | Survival To D-stage (%) | Survival To Spat (%) |
|---|---|---|---|---|
| DD | 97.0 | 2,688 | 32.2 | 0.89 |
| DT | 92.3 | 2,986 | 11.4 | 0.50 |
| TD | 97.5 | 2,465 | 29.3 | 0.87 |
| TT | 97.8 | 2,442 | 9.5 | 0.001 |

The above procedure is repeated using tetraploid *Crassostrea virginica* oysters of this invention and diploid *Crassostrea virginia* oysters. Good yields of DT and TD crosses of triploid *Crassostrea virginica* oysters are obtained.

Figure 2:
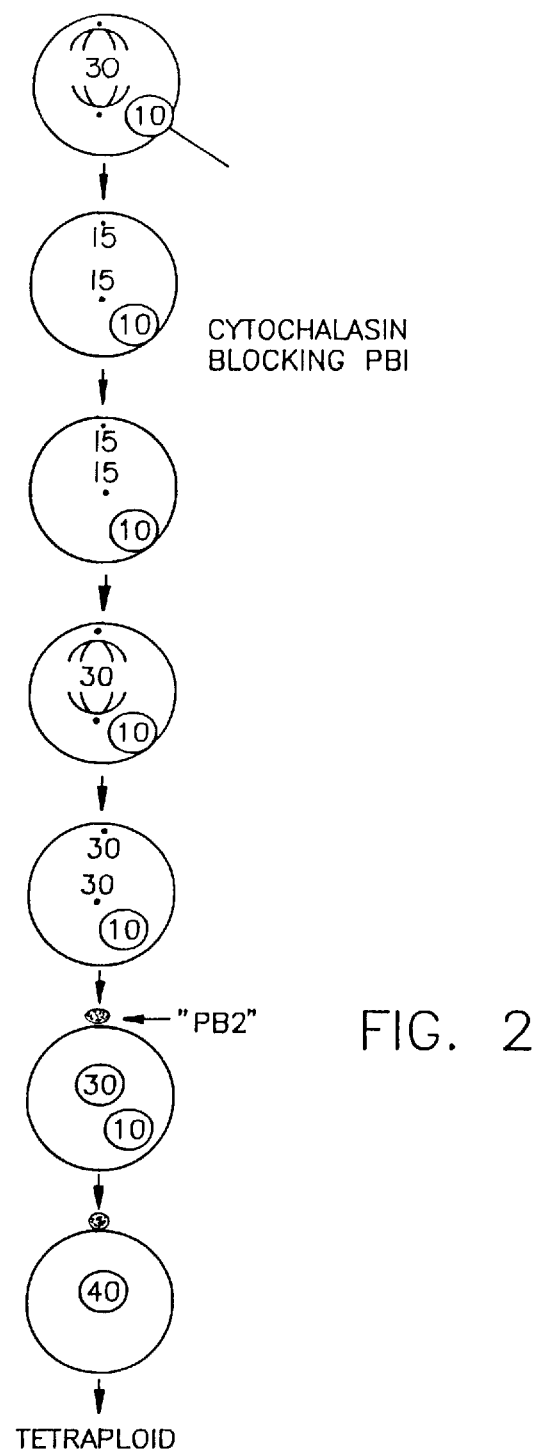
FIG. 2 schematically depicts various biological events which are believed to be taking place leading to the formation of a tetraploid oyster from a triploid female and a diploid male by virtue of PB1 blocking.

Various biological events which are believed to be taking place in the above-described method of this invention leading to the formation of a tetraploid oyster from a triploid female and a diploid male by virtue of PB1 blocking are schematically depicted in FIG. 2. These events should be contrasted with the usual situation depicted in FIG. 1.

The production of viable tetraploids with eggs obtained from triploids as demonstrated above supports the cell-number deficiency hypothesis. The eggs from triploids were 54% larger in volume than those obtained from diploids, and the increased egg volume probably led to a significant increase in cell numbers.

Once mature tetraploid oysters are produced according to this invention, they can be used to mate with normal diploid oysters to create triploids—4n×2n–>3n. Briefly, because triploids are reproductively less competent than normal diploids, they have certain physiological advantages that translate into increased market benefit for the commercial producers (Allen, 1988). Triploid oysters are cultured widely on the West Coast and increasingly on the East Coast of the USA. Triploids are also cultured in Europe (e.g., France, Ireland) and Asia (e.g., Japan, China, Korea).

An important feature of the current commercial production of triploids is that they are produced with the use of the antibiotic cytochalasin B (CB). CB has been found to be teratogenic and mutagenic in numerous human and animal studies. Because it is used on oyster eggs, CB is not present in market sized oysters, so there is no risk of tissue residue. However, the inherent toxicity of this drug has prompted the Department of Health and Human Services' Center for Veterinary Medicine to place CB on "not low regulatory priority." Presumably other countries will have similar concerns about the use of CB and other chemicals. The new route of producing triploid oysters from tetraploids which route is afforded by this invention will obviate this concern worldwide.

There are at least three other advantages of creating triploids by mating versus inducing (with drugs or other procedures). (i) Triploids produced by mating tetraploids with diploids may prove to be more robust than triploids produced by drug treatment because the size of the tetraploid eggs will be much larger than diploid eggs. (The egg size of triploids is about 1.5 times the volume of diploid eggs. Tetraploids may have eggs twice the size of diploids.) The increased egg size is advantageous because it gives the developing embryo more energetic reserves early in the larval cycle. In carrying out this invention, there has been evidence that tetraploid shellfish produce gametes, and that eggs of tetraploids are larger. (ii) Triploids produced from 4n×2n matings will be free of inbreeding depression due to inhibition of the second polar body. (iii) Theoretically, the progeny of 4n×2n matings will be 100% triploid, a degree of success never obtained by inducing triploidy. The advantage of a pure triploid crop, versus one contaminated with an indeterminate number of diploids and mosaics, is very significant. Pure triploid crops will also be advantageous for population control. Since a triploid population would be functionally sterile (3n×3n matings are inviable), they can be used to obviate reproduction in the ecosystem, such as with non-native species or genetically modified organisms.

Tetraploid shellfish are themselves potential candidates for aquaculture. Preliminary observation conducted by the present inventors has shown that tetraploid oysters have an abnormally large adductor muscle, which is the market product in scallops.

Besides the advantages and applications of the tetraploids described above, there are many others. Thus, tetraploids can be used to make bridging crosses between two species that normally do not hybridize. Tetraploids also will be useful for creating more tetraploids, 4n×4n–>4n. Tetraploids could be used to create unique diploid combinations through a process known as gynogenesis. Other advantages and applications of the present invention will be apparent to people skilled in the art after careful reading of the instant disclosure.

Although the foregoing description of this invention has been presented with a primary emphasis on a preferred embodiment of the invention, the scope of the invention is not limited in any way to the preferred embodiment, but instead it is defined only by the claims appended to this specification.

As mentioned earlier, brief definitions of certain technical terms are presented below in order to aid the understanding of the instant invention.

Aneuploid: A form in which one or more individual chromosomes (as opposed to the entire set of chromosomes) have been lost or gained as compared to the normal diploid.

Centromere: A constructed region of a chromosome that includes the site of attachment to the mitotic meiotic spindle.

Chromatids: Copies of a chromosome produced by replication.

Diploid: A form possessing a set of chromosomes which is double the basic number (n), the haploid number.

Euploid: A form possessing an integral number of the basic set of chromosomes.

Haploid: A form possessing the basic set of chromosomes.

Meiosis: A special process of cell division occurring in maturation of the sex cells whereby each daughter nucleus receives half the number of chromosomes. It is therefore the opposite of fertilization. It compensates for the doubling of the chromosome number brought about at fertilization under normal situation Mitosis: A division of cell nucleus in which a spindle and chromosomes are involved. The process results in two daughter nuclei which are identical to each other and to the original nucleus.

Tetraploid: A form possessing a set of chromosomes which is four times the haploid number.

Triploid: A form possessing a set of chromosomes which is three times the haploid number.

REFERENCES

Allen, Jr., S. K. (1988); Oceanus 31, 58–63.

Allen, Jr., S. K. and Downing, S. L. (1991); J. Shellfish Research 10, 19–22.

Guo, X. (1991); Ph.D. Dissertation, University of Washington, Seattle, Wash.

Guo, X., Cooper, K., Hershberger, W. K. and Chew, K. K. (1992a); Biol. Bull. 183 381–386.

Guo, X., Hershberger, W. K., Cooper, K. and Chew, K. K. (1992b); Biol. Bull. 183, 387–393.

Guo, X., Hershberger, W. K., Cooper, K. and Chew, K. K. (1993); Aquaculture 113 201–214.

Lu, J.-K. (1986): M.S. Thesis, University of Washington, Seattle, Wash.

Perdue, J. A. (1983); Ph.D. Dissertation, University of Washington, Seattle, Wash.

Quayle, D. B. (1988); Can. Bull. Fish. Aquat. Sci., 218, 1–241.

Stephens, L. B. and Downing, S. L. (1989); J. Shellfish Research 8(1), 324.

What is claimed is:

1. A viable tetraploid oyster which can grow and mature under natural conditions that a corresponding normal diploid oyster can naturally habit, wherein said tetraploid oyster can be mated with a diploid oyster to produce a triploid oyster.

2. The oyster of claim 1, wherein the oyster belongs to the species *Crassostrea gigas* Thunberg.

3. The oyster of claim 1 that belongs to a species selected from the group consisting of *Crassostrea sikamai, Crassostrea rivularis* and *Crassostrea virginica*.

4. The viable tetraploid oyster of claim 1 produced by fertilizing an egg from a triploid female oyster with a sperm from a diploid male oyster and blocking the release of polar body I from the fertilized egg.

5. The oyster of claim 4, wherein the oyster belongs to the species *Crassostrea gigas* Thunberg.

6. The oyster of claim 4, wherein the oyster belongs to a species selected from the group consisting of *Crassostrea sikamai, Crassostrea rivularis* and *Crassostrea virginica*.

7. The oyster of claim 4, wherein the oyster is a pearl oyster.

8. The oyster of claim 7, wherein said oyster belongs to the species *Pinctada magaratifera*.

9. The oyster of claim 1, wherein the oyster is a pearl oyster.

10. The oyster of claim 9, wherein said oyster belongs to the species *Pinctada magaratifera*.

11. The tetraploid oyster of claim 1 produced by mating a tetraploid female oyster and a tetraploid male oyster.

12. The tetraploid oyster of claim 11, wherein the oyster produced belongs to the species *Crassostrea gigas* Thunberg.

13. The tetraploid oyster of claim 11, wherein said oyster belongs to a species selected from the group consisting of *Crassostrea sikamai, Crassostrea rivularis* and *Crassostrea virginica*.

14. The method of claim 11, wherein the oyster is a pearl oyster.

15. The method of claim 14, wherein said oyster belongs to the species *Pinctada magaratifera*.

16. A method of producing a viable tetraploid oyster which comprises (i) fertilizing an egg from a triploid female oyster with a sperm from a diploid male oyster, (ii) blocking the release of polar body I from the fertilized egg, and (iii) cultivating the fertilized egg, whereby a viable tetraploid oyster is produced.

17. The method of claim 16, wherein the oyster belongs to the species *Crassostrea gigas* Thunberg.

18. The method of claim 17, wherein the blocking of polar body I is carried out with the aid of cytochalasin B.

19. The method of claim 16, wherein the oyster belongs to a species selected from the group consisting of *Crassostrea sikamai, Crassostrea rivularis* and *Crassostrea virginica*.

20. The method of claim 19, wherein the blocking of polar body I is carried out with the aid of cytochalasin B.

21. The method of claim 16, wherein the blocking of polar body I is carried out with the aid of cytochalasin B.

22. The method of claim 16, wherein the oyster is a pearl oyster.

23. The method of claim 22, wherein said oyster belongs to the species *Pinctada magaratifera*.

24. The method of claim 23, wherein the blocking of polar body I is carried out with the aid of cytochalasin B.

25. The method of claim 22, wherein the blocking of polar body I is carried out with the aid of cytochalasin B.

26. A method of producing a tetraploid oyster which comprises mating a tetraploid female oyster with a tetraploid male oyster.

27. The method of claim 26, wherein the oyster produced belongs to the species *Crassostrea gigas* Thunberg.

28. The method of claim 26 wherein said oyster produced belongs to a species selected from the group consisting of *Crassostrea sikamai, Crassostrea rivularis* and *Crassostrea virginica*.

29. The method of claim 26, wherein the oyster is a pearl oyster.

30. The method of claim 29, wherein said oyster belongs to the species *Pinctada magaratifera*.

31. A method of producing a triploid oyster which comprises mating a tetraploid oyster with a diploid oyster.

32. The method of claim 31, which comprises fertilizing an egg of a diploid female oyster with sperm of a tetraploid male oyster.

33. The method of claim 32, wherein the oyster produced belongs to the species *Crassostrea gigas* Thunberg.

34. The method of claim 32 wherein said oyster produced belongs to a species selected from the group consisting of *Crassostrea sikamai, Crassostrea rivularis* and *Crassostrea virginica*.

35. The method of claim 32, wherein the oyster is a pearl oyster.

36. The method of claim 35, wherein said oyster belongs to the species *Pinctada magaratifera*.

* * * * *